US009035794B2

(12) United States Patent
Narasimhan et al.

(10) Patent No.: US 9,035,794 B2
(45) Date of Patent: May 19, 2015

(54) POSTURE CALIBRATION FOR ACTIVITY MONITORING (75) Inventors: Ravi Narasimhan, Sunnyvale, CA (US); Nima Ferdosi, San Jose, CA (US)

(73) Assignee: VITAL CONNECT, INC., Campbell, CA (US)

( * ) Notice: Subject to any disclaimer, the term of this patent is extended or adjusted under 35 U.S.C. 154(b) by 349 days.

(21) Appl. No.: 13/548,059

(22) Filed: Jul. 12, 2012

(65) Prior Publication Data

US 2014/0015687 A1    Jan. 16, 2014

(51) Int. Cl.
*G08B 29/00* (2006.01)
*G01C 25/00* (2006.01)
*G08C 17/02* (2006.01)
*A61B 5/00* (2006.01)
*A61B 5/11* (2006.01)
*G01N 33/48* (2006.01)
*A61N 1/00* (2006.01)
*G06T 15/00* (2011.01)
*A61B 5/103* (2006.01)

(52) U.S. Cl.
CPC ............... *G01C 25/00* (2013.01); *G08C 17/02* (2013.01); *G01C 25/005* (2013.01); *A61B 5/0002* (2013.01); *A61B 5/1116* (2013.01); *A61B 5/1118* (2013.01)

(58) Field of Classification Search
USPC ............ 340/870.2; 702/19; 607/62; 345/419; 600/595
See application file for complete search history.

(56) References Cited

U.S. PATENT DOCUMENTS

| 6,044,297 | A | 3/2000 | Sheldon et al. |
|---|---|---|---|
| 2007/0115277 | A1* | 5/2007 | Wang et al. ................... 345/419 |
| 2010/0010583 | A1* | 1/2010 | Panken et al. ................... 607/62 |
| 2010/0298655 | A1* | 11/2010 | McCombie et al. .......... 600/301 |
| 2011/0172927 | A1* | 7/2011 | Sahasrabudhe et al. ......... 702/19 |
| 2011/0201969 | A1 | 8/2011 | Hatlestad et al. |
| 2011/0241656 | A1 | 10/2011 | Piemonte et al. |
| 2012/0101411 | A1* | 4/2012 | Hausdorff et al. ............ 600/595 |
| 2013/0274830 | A1* | 10/2013 | Skelton ........................... 607/62 |

* cited by examiner

*Primary Examiner* — Jack K Wang
(74) *Attorney, Agent, or Firm* — Sawyer Law Group, P.C.

(57) ABSTRACT

A method and system for activity monitoring of a user are disclosed. In a first aspect, the method comprises calibrating posture by the user to determine a calibration vector. The method includes validating the calibration vector by comparing an anteroposterior axis to a threshold, wherein activity of the user is monitored using the validated calibration vector. In a second aspect, a wireless sensor device comprises a processor and a memory device coupled to the processor, wherein the memory device includes an application that, when executed by the processor, causes the processor to receive a posture calibration request from the user and to determine a calibration vector based on the received request. The application, when executed by the processor, further causes the processor to validate the calibration vector by comparing an anteroposterior axis to a threshold, wherein activity of the user is monitored using the validated calibration vector.

18 Claims, 6 Drawing Sheets

POSTURE CALIBRATION FOR ACTIVITY MONITORING

FIELD OF THE INVENTION

The present invention relates to wireless sensor devices, and more particularly, to using a wireless sensor device to calibrate posture for activity monitoring.

BACKGROUND

Wireless sensor devices are used in a variety of applications including the activity monitoring of users. In many of these applications, a wireless sensor device is attached directly to the user's skin to measure certain data. This measured data is then utilized for the activity monitoring of the users. Therefore, there is a strong need for a cost-effective solution that more accurately calibrates posture for the activity monitoring of a user. The present invention addresses such a need.

SUMMARY OF THE INVENTION

A method and system for activity monitoring of a user are disclosed. In a first aspect, the method comprises calibrating posture by the user to determine a calibration vector. The method includes validating the calibration vector by comparing an anteroposterior axis to a threshold, wherein activity of the user is monitored using the validated calibration vector.

In a second aspect, a wireless sensor device comprises a processor and a memory device coupled to the processor, wherein the memory device includes an application that, when executed by the processor, causes the processor to receive a posture calibration request from the user and to determine a calibration vector based on the received request. The application, when executed by the processor, further causes the processor to validate the calibration vector by comparing an anteroposterior axis to a threshold, wherein activity of the user is monitored using the validated calibration vector.

BRIEF DESCRIPTION OF THE DRAWINGS

The accompanying figures illustrate several embodiments of the invention and, together with the description, serve to explain the principles of the invention. One of ordinary skill in the art readily recognizes that the particular embodiments illustrated in the figures are merely exemplary, and are not intended to limit the scope of the present invention.

DETAILED DESCRIPTION

The present invention relates to wireless sensor devices, and more particularly, to using a wireless sensor device to calibrate posture for activity monitoring. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A method and system in accordance with the present invention automatically calibrates a user's posture for activity monitoring. By attaching a wireless sensor device in any orientation and in any bodily location to the user and comparing a calibration vector to a vertical posture, a user's posture is automatically calibrated and used in algorithms that measure activity level including but not limited to pedometer activity, fall detection, and posture detection.

One of ordinary skill in the art readily recognizes that a variety of wireless sensor devices can be utilized including but not limited to tri-axial accelerometers, uni-axial accelerometers, bi-axial accelerometers, gyroscopes, and pressure sensors and that would be within the spirit and scope of the present invention.

To describe the features of the present invention in more detail, refer now to the following description in conjunction with the accompanying Figures.

In one embodiment, a wireless sensor device is attached to a user and continuously and automatically obtains varying types of data including but not limited to acceleration samples along an anteroposterior axis of the user. An application embedded within a processor of the wireless sensor device compares the acceleration samples to a threshold to monitor the user's activity including but not limited to pedometer activity, fall detection, and posture detection.

Figure 1:
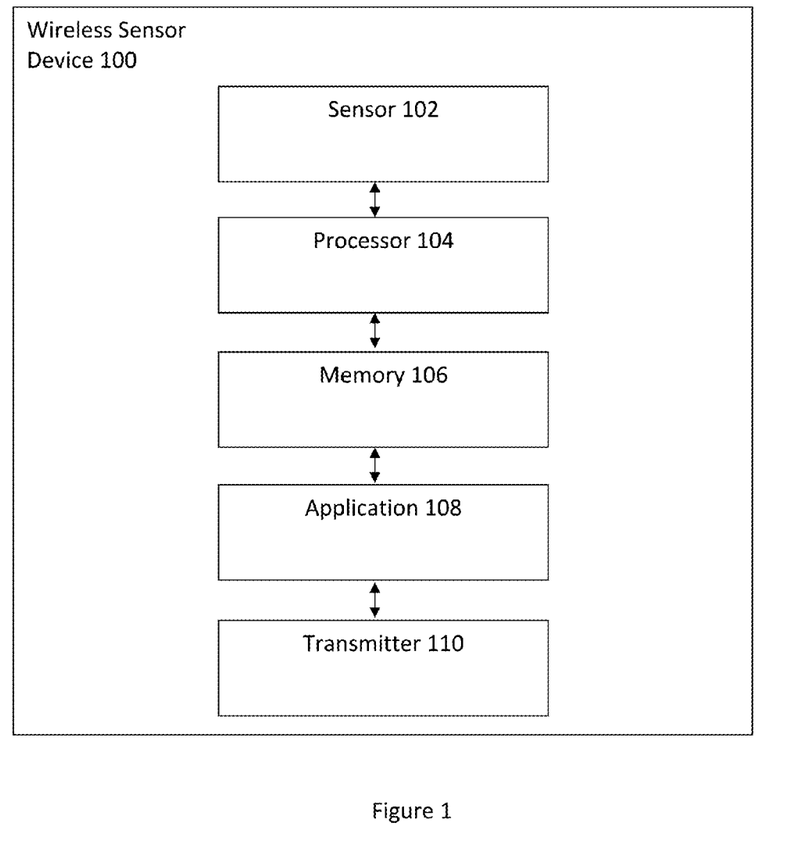
FIG. 1 illustrates a wireless sensor device in accordance with an embodiment.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached, in any orientation to a user and on any location of the user. The sensor 102 obtains data from the user and transmits the data to the memory 106 and in turn to the application 108. The processor 104 executes the application 108 to monitor information regarding the user's activity. The information is transmitted to the transmitter 110 and in turn relayed to another user or device.

In one embodiment, the sensor 102 is a microelectromechanical system (MEMS) tri-axial accelerometer and the processor 104 is a microprocessor. One of ordinary skill in the art readily recognizes that a variety of devices can be utilized for the processor 104, the memory 106, the application 108, and the transmitter 110 and that would be within the spirit and scope of the present invention.

Figure 2:
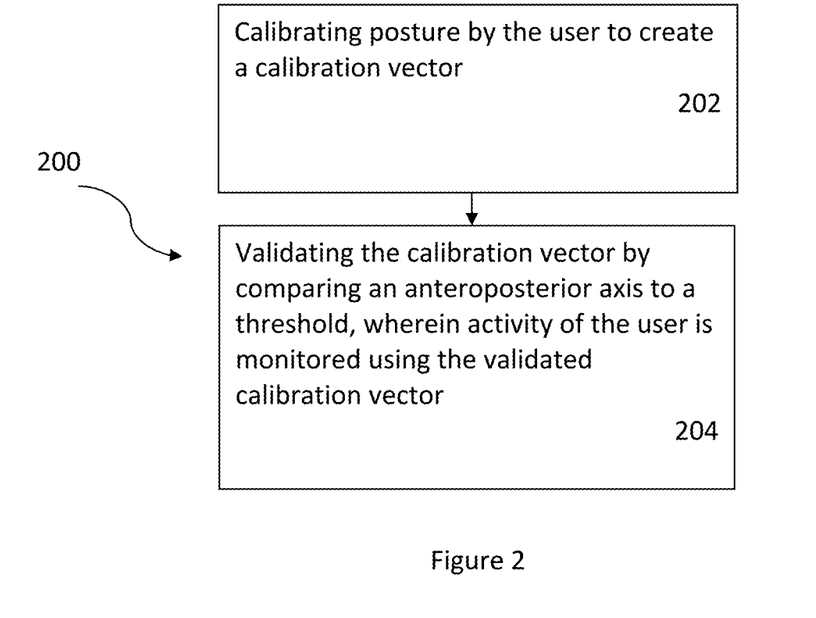
FIG. 2 illustrates a flow chart of a method in accordance with an embodiment.

FIG. 2 illustrates a flow chart of a method 200 in accordance with an embodiment. Referring to FIGS. 1 and 2 together, the method 200 comprises calibrating posture by the user to determine a calibration vector, via step 202. The wireless sensor device 100 validates the calibration vector by comparing an anteroposterior axis to a threshold and monitors the activity of the user using the validated calibration vector, via step 204. In one embodiment, the sensor 102 that is housed within the wireless sensor device 100 measures the anteroposterior axis of the user. In another embodiment, notification information of the activity monitoring of the user is relayed by the wireless sensor device 100 to another user or device.

Figure 3:
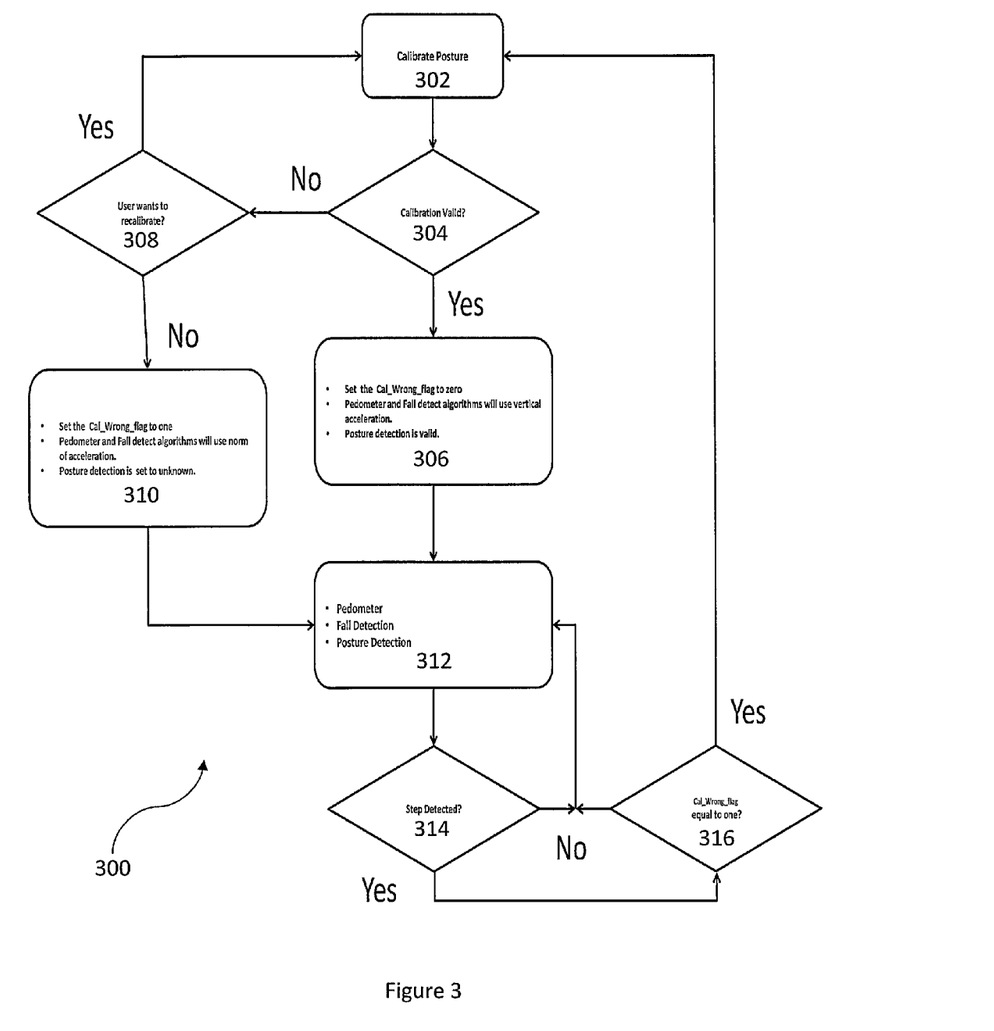
FIG. 3 illustrates a more detailed flow chart of a method in accordance with an embodiment.

FIG. 3 illustrates a more detailed flow chart of a method 300 in accordance with an embodiment. A wireless sensor device is attached to a user in any orientation and on any bodily location of the user. Referring to FIGS. 1 and 3 together, the method 300 comprises an explicit calibration of the user's posture to determine a calibration vector, via step 302. In one embodiment, calibrating the user's posture explicitly includes but is not limited to the user notifying the wireless sensor device 100 when the user is in a vertical position and the wireless sensor device 100 being attached to the user's chest when the user is in a vertical position.

In this embodiment, the user notifies the wireless sensor device 100 in a variety of ways including but not limited to tapping the wireless sensor device 100, selecting a button of the wireless sensor device 100, and interacting with a mobile application interface of the wireless sensor device 100. Furthermore, in this embodiment, when the wireless sensor device 100 is attached to the user's chest while the user is in a vertical position, the wireless sensor device 100 recognizes contact impedance to confirm attachment between the user and the wireless sensor device 100.

The wireless sensor device 100 checks to see whether the explicitly determined calibration vector is valid, via step 304. If the determined calibration vector is valid, the wireless sensor device 100 sets cal_wrong_flag to zero (0), uses a vertical acceleration based on the validated calibration vector in both pedometer activity and fall detection algorithms, and confirms posture detection is valid, via step 306.

In FIG. 3, if the explicitly determined calibration vector is not valid, the wireless sensor device 100 displays a validation failure message to the user prompting the user to determine whether the user wants to explicitly recalibrate another calibration vector, via step 308. If the user wants to explicitly recalibrate another calibration vector, the method 300 returns back to step 302. If the user does not want to explicitly recalibrate another calibration vector, the method 300 sets cal_wrong_flag to one (1), uses a norm of acceleration in both pedometer activity and fall detection algorithms, and sets posture detection to unknown, via step 310. In this embodiment, when the determined calibration vector is not valid, the wireless sensor device 100 monitors the activity of the user using a set of algorithms that are independent of the calibration vector.

In one embodiment, the determined calibration vector is checked for validity by ensuring a magnitude of acceleration along an anteroposterior axis of the user is less than a predetermined threshold including but not limited to $g*\sin(\pi/6)$, where g is the acceleration due to gravity. In this embodiment, if the magnitude of acceleration along the anteroposterior axis of the user is less than the predetermined threshold, then the calibration vector is determined to be valid and the method 300 proceeds to step 306. However, if the magnitude of acceleration along the anteroposterior axis of the user is greater than or equal to the predetermined threshold, then the calibration vector is determined to be invalid and the method 300 proceeds to step 308. The anteroposterior axis of the user measures the axis from the front chest to the back of the user and is nearly perpendicular to gravity when the user is in a vertical posture.

Figure 4:
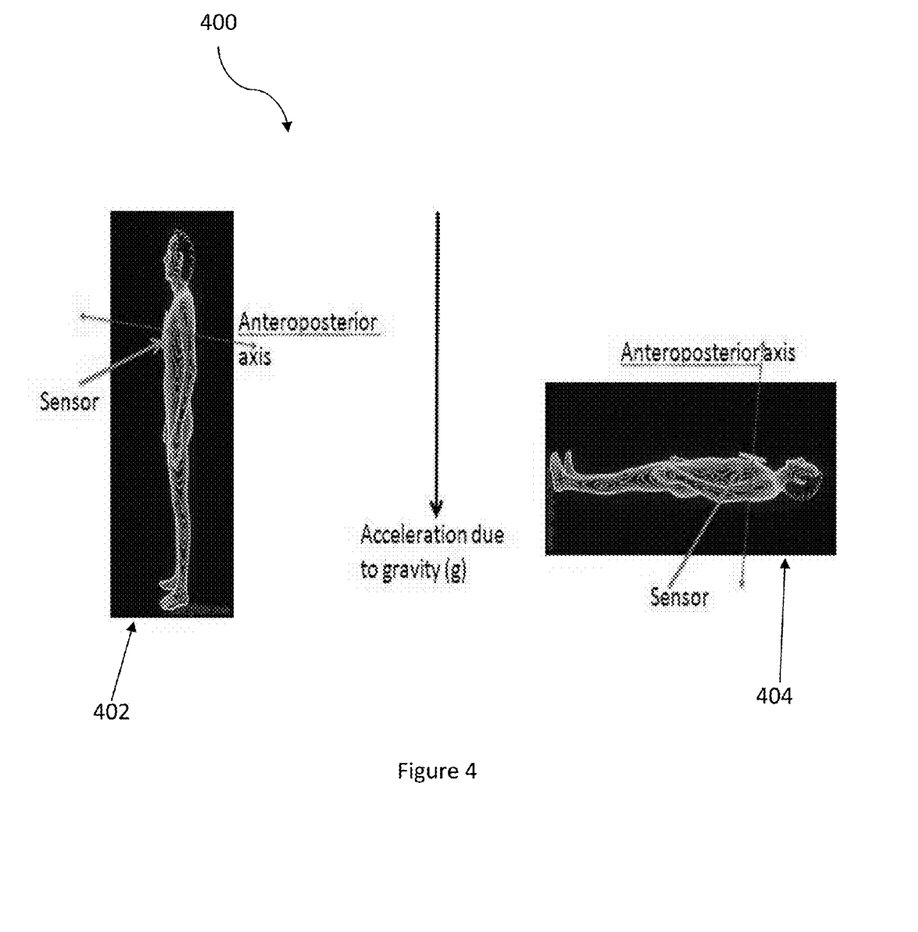
FIG. 4 illustrates a diagram of calibration vector checking in accordance with an embodiment.

FIG. 4 illustrates a diagram 400 of calibration vector checking in accordance with an embodiment. The diagram 400 includes a first scenario 402 where the calibration check passes because an absolute value of acceleration along the anteroposterior axis of the user is less than the predetermined threshold. The diagram 400 includes a second scenario 404 where the calibration check fails because an absolute value of acceleration along the anteroposterior axis of the user is greater than or equal to the predetermined threshold.

Referring back to FIG. 3, after both steps 310 and 306, the user's activity including but not limited to pedometer activity, fall detection, and posture detection is monitored using various algorithms depending upon whether the calibration vector is validated or not, via step 312. In one embodiment, monitoring the activity of the user using the validated calibration vector includes but is not limited to monitoring pedometer activity using a vertical component of an acceleration vector of the user, monitoring fall detection using p-norm of the acceleration vector to detect an impact and an angle of the acceleration vector with respect to the validated calibration vector thereby determining a horizontal position of the user after impact, and monitoring posture detection using both the acceleration vector and the validated calibration vector.

In another embodiment, monitoring the activity of the user using a non-validated calibration vector due to a validation failure includes but is not limited to monitoring pedometer activity using 2-norm of an acceleration vector of the user and monitoring fall detection using p-norm of the acceleration vector to detect an impact. In this embodiment, the monitoring of fall detection does not compute an angle and the posture of the user is unknown. Accordingly, it is desirable to monitor the activity of the user using a validated calibration vector.

Therefore, the activity algorithms utilized by the wireless sensor device 100 vary when using a validated calibration vector and when not using a validated calibration vector. In one embodiment, current acceleration (a) and calibration vectors (c) are utilized by the wireless sensor device 100 in the activity algorithms with a=(ax, ay, az) and c=(cx, cy, cz) when the calibration vector is validated.

In this embodiment, the activity algorithms that include a validated calibration vector comprise a pedometer activity algorithm that is based on a vertical component of the acceleration vector (pedometer activity (v)=a·c=ax*cx+ay*cy+az*cz), a fall detection algorithm that is based on p-norm of a to detect an impact and angle of a with respect to c to determine a horizontal position of the user after impact (p-norm of a=(|ax|^p+|ay|^p+|az|^p)^(1/p), for p>=1; angle of a computed using a·c and 2-norms of a and c), and a posture detection algorithm that is based on a·c, cz and az.

Furthermore, in another embodiment, the activity algorithms that are utilized by the wireless sensor device 100 when not using a validated calibration vector include but are not limited to a pedometer activity algorithm that is based on 2-norms of a, a fall detection algorithm that is based on p-norm of a to detect an impact where no angle of a is computed, and no posture detection algorithm because the posture of the user is unknown.

In the method 300, once footsteps of the user are detected by a pedometer type device that has been integrated into the wireless sensor device 100, via step 314, the wireless sensor device 100 utilizes implicit calibration to determine a new calibration vector. In one embodiment, the implicit calibration includes but is not limited to the wireless sensor device 100 deriving a vertical position based on an acceleration vector corresponding to footsteps when the user is walking. After the implicit calibration, the method 300 checks to see whether cal_wrong_flag is equal to one (1), via step 316.

If cal_wrong_flag is equal to one (1) indicating that the wireless sensor device 100 has been monitoring the activity of the user using a non-validated calibration vector, the method 300 returns back to step 302 to validate the new calibration vector. If cal_wrong_flag is not equal to one (1), indicating that the wireless sensor device 100 has been monitoring the activity of the user using a validated calibration vector, the method 300 returns back to step 312 and the wireless sensor device 100 continues the activity monitoring of the user.

Figure 5:
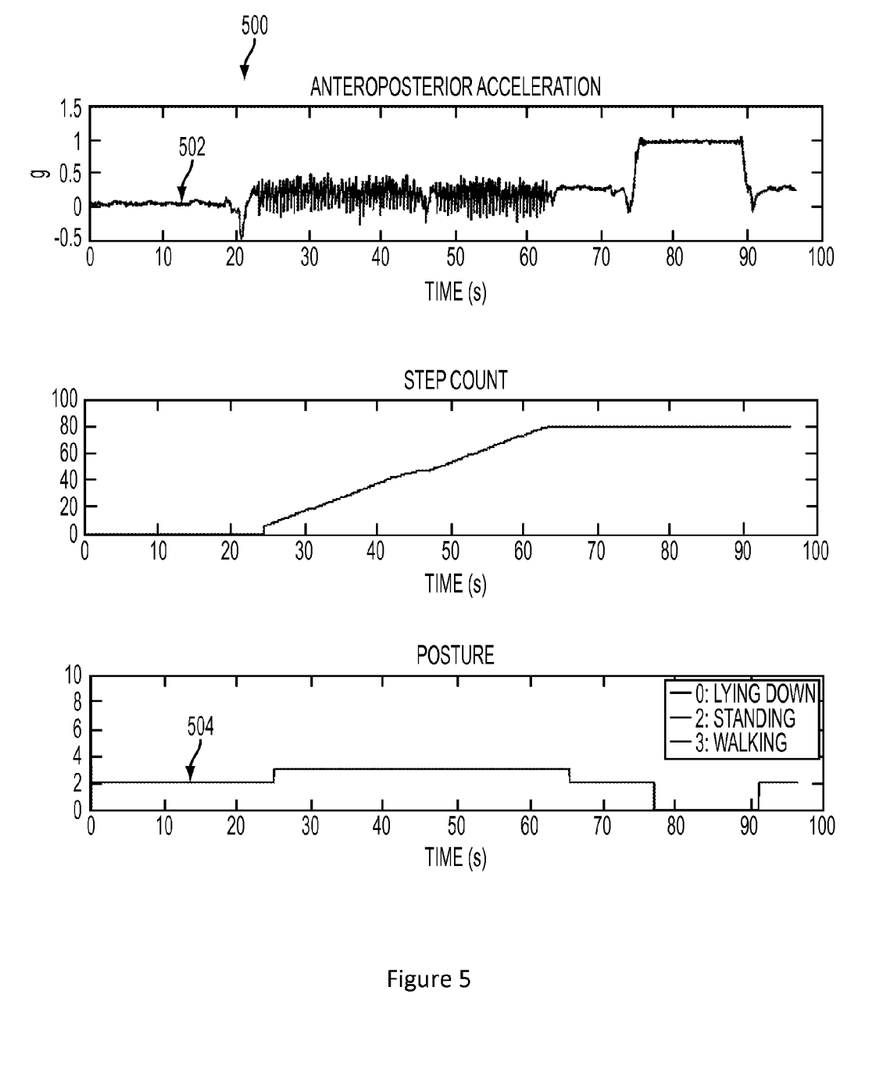
FIG. 5 illustrates a diagram of an example of explicit calibration in accordance with an embodiment.

FIG. 5 illustrates a diagram 500 of an example of explicit calibration in accordance with an embodiment. The diagram 500 plots anteroposterior acceleration, step count, and posture of the user over a predetermined time period. The diagram 500 starts with a valid explicit calibration 502 corresponding to a known standing posture 504 of the user. The explicit calibration is valid because the user is in a standing posture when the user has notified the wireless sensor device to explicitly calibrate or the wireless sensor device has been attached to the user while in a standing posture.

As the step count of the user increases, the anteroposterior acceleration fluctuates and the posture of the user is identified to be in a walking posture. At approximately sixty (60) seconds, the step count of the user doesn't increase anymore thereby illustrating another change in the user's posture.

Figure 6:
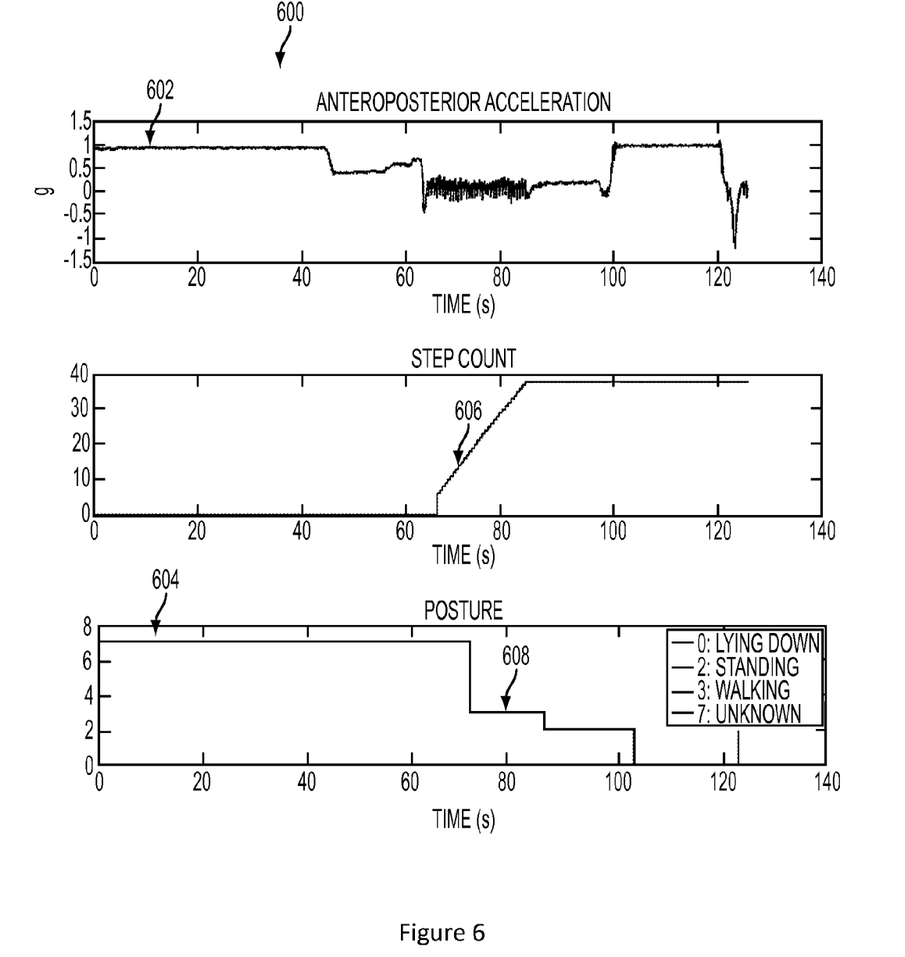
FIG. 6 illustrates a diagram of an example of implicit calibration in accordance with an embodiment.

FIG. 6 illustrates a diagram 600 of an example of implicit calibration in accordance with an embodiment. The diagram 600 plots anteroposterior acceleration, step count, and posture of the user over a predetermined time period. The diagram 600 starts with an invalid explicit calibration 602 corresponding to an unknown posture 604 of the user. The explicit calibration is invalid because the user is in an unknown posture when the user has notified the wireless sensor device to explicitly calibrate or the wireless sensor device has not been attached to the user while in a standing posture.

As aforementioned, due to this invalid explicit calibration, the wireless sensor device attached to the user will monitor the user's activity by utilizing activity algorithms that do not incorporate a calibration vector. As the step count of the user increases, implicit calibration while walking 606 occurs to incorporate a newly determined calibration vector into the activity algorithms utilized by the wireless sensor device. At this time while the user is walking, which is at approximately seventy (70) seconds, the wireless sensor device computes a known posture of the user 608.

As above described, the method and system allow for activity monitoring based upon automatic posture calibration. By implementing a tri-axial accelerometer within a wireless sensor device to detect acceleration and posture samples and an application located on the wireless sensor device to process the detected acceleration and posture samples, an efficient and cost-effective activity monitoring system is achieved that can support various types of activities and can confirm changes in a user's posture.

A method and system for activity monitoring of a user have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for activity monitoring of a user, the method comprising:
   calibrating posture by the user to determine a calibration vector; and
   validating the calibration vector by comparing an anteroposterior axis to a threshold, wherein activity of the user is monitored by any of:
   pedometer activity using a vertical component of an acceleration vector of the user;
   fall detection using p-norm of an acceleration vector of the user to detect an impact and an angle of the acceleration vector with respect to the validated calibration vector thereby determining a horizontal position of the user after impact; and
   posture detection using both an acceleration vector of the user and the validated calibration vector.

2. The method of claim 1, further comprising:
   in response to a validation failure, monitoring the activity of the user independent of the calibration vector and reporting an unknown posture for the user; and
   calibrating the posture implicitly when the user is walking.

3. The method of claim 2, further comprising:
   in response to the validation failure, determining whether to recalibrate the posture explicitly.

4. The method of claim 1, wherein the validating further comprises:
   ensuring a magnitude of acceleration along the anteroposterior axis is less than the threshold.

5. The method of claim 2, wherein the validation failure occurs when a magnitude of acceleration along the anteroposterior axis is greater than or equal to the threshold.

6. The method of claim 1, wherein calibrating the posture further comprises any of the user notifying a wireless sensor device when the user is in a vertical position and the user placing the wireless sensor device on the user's chest when the user is in a vertical position.

7. The method of claim 6, wherein the notifying further comprises any of tapping of the wireless sensor device, selecting a button of the wireless sensor device, and interacting with a mobile application interface of the wireless sensor device.

8. The method of claim 6, further comprising:
   in response to the placing, recognizing contact impedance to show attachment by the wireless sensor device.

9. The method of claim 2, wherein calibrating the posture implicitly further comprises deriving a vertical position by a wireless sensor device based on an acceleration vector corresponding to footsteps when the user is walking.

10. The method of claim 2, wherein the monitoring the activity of the user independent of the calibration vector further comprises any of:
   monitoring pedometer activity using 2-norm of an acceleration vector of the user; and
   monitoring fall detection using p-norm of the acceleration vector to detect an impact.

11. The method of claim 1, further comprising:
   attaching a wireless sensor device to the user in any orientation and on any location.

12. The method of claim 1, further comprising:
   relaying notification information of the activity monitoring of the user to another user or device.

13. A wireless sensor device for activity monitoring of a user, the wireless sensor device comprising:
   a processor; and
   a memory device coupled to the processor, wherein the memory device includes an application that, when executed by the processor, causes the processor to:
   receive a posture calibration request from the user;
   determine a calibration vector based on the received request; and
   validate the calibration vector by comparing an anteroposterior axis to a threshold, wherein activity of the user is monitored by any of:
      pedometer activity using a vertical component of an acceleration vector of the user;
      fall detection using p-norm of an acceleration vector of the user to detect an impact and an angle of the acceleration vector with respect to the validated calibration vector thereby determining a horizontal position of the user after impact; and
      posture detection using both an acceleration vector of the user and the validated calibration vector.

14. The wireless sensor device of claim 13, wherein the application, when executed by the processor, further causes the processor to:
   in response to a validation failure, monitor the activity of the user independent of the calibration vector and report an unknown posture for the user; and
   calibrate the posture implicitly when the user is walking.

15. The wireless sensor device of claim 13, wherein to validate further comprises to ensure a magnitude of acceleration along the anteroposterior axis is less than the threshold.

16. The wireless sensor device of claim 14, wherein the validation failure occurs when a magnitude of acceleration along the anteroposterior axis is greater than or equal to the threshold.

17. The wireless sensor device of claim 14, wherein to monitor the activity of the user independent of the calibration vector further comprises causing the processor to perform any of:
   monitoring pedometer activity using 2-norm of an acceleration vector of the user; and
   monitoring fall detection using p-norm of the acceleration vector to detect an impact.

18. The wireless sensor device of claim 13, wherein the application, when executed by the processor, further causes the processor to:
   relay notification information of the activity monitoring of the user to another user or device.

* * * * *